United States Patent
Stauder et al.

(12) 
(10) Patent No.: US 6,280,728 B1
(45) Date of Patent: Aug. 28, 2001

(54) TREATMENT OF HEPATITIS C VIRUS INFECTION USING A PROTEASE AND A FLAVONOID

(75) Inventors: Gerhard Stauder, Geretsried; Karl Ransberger, Seeshaupt, both of (DE)

(73) Assignee: Mucos Pharma GmbH & Co. (DE)

( * ) Notice: Subject to any disclaimer, the term of this patent is extended or adjusted under 35 U.S.C. 154(b) by 0 days.

(21) Appl. No.: 09/245,820

(22) Filed: Feb. 5, 1999

(30) Foreign Application Priority Data

Feb. 6, 1998 (DE) ................................................ 198 04 742

(51) Int. Cl.⁷ ...................................................... A61K 38/48
(52) U.S. Cl. ..................... 424/94.64; 424/94.65; 514/25; 514/21; 514/27
(58) Field of Search .................. 424/94.1, 94.2, 424/94.64, 94.65; 514/25, 27, 685, 894, 21, 53, 177

(56) References Cited

PUBLICATIONS

Kabil et al., Oral enzyme therapy in hepatitis C patients. International Journal of Tissue Reactions 19(1/2): 97–98, 1997.*

Stedman's Medical Dictionary, Williams & Wilkins, 1995.*

G. Stauder, et al., "Oral Enzyme Therapy In Hepatitis C Patients", International Journal of Immunotherapy XIII(3/4) pp. 153–158 (1997)—published Mar. 1998.

* cited by examiner

Primary Examiner—Donna C. Wortman
(74) Attorney, Agent, or Firm—Akin, Gump, Strauss, Hauer & Feld, L.L.P.

(57) ABSTRACT

The use of at least one hydrolytic enzyme and at least one flavonoid shows better activity than α-interferon or ribavirin in the treatment of diseases caused by hepatitis C viruses.

6 Claims, 4 Drawing Sheets

TREATMENT OF HEPATITIS C VIRUS INFECTION USING A PROTEASE AND A FLAVONOID

CROSS-REFERENCE TO RELATED APPLICATIONS

This application is entitled to priority pursuant to 35 U.S.C. §119 to German patent application 198 04 742.8, filed Feb. 6, 1998.

BACKGROUND OF THE INVENTION

The present invention relates to the use of at least one hydrolytic enzyme and at least one flavonoid for the treatment of diseases caused by hepatitis C viruses.

Hepatitis is an inflammation of the liver, which can arise on account of various causes. The acute forms of hepatitis are mostly caused by viruses. At present, six different types of hepatitis virus are known (A–E and G). Hepatitis C is a viral disease in which persistence of the hepatitis C virus or chronic hepatitis can ensue. This chronic hepatitis C develops in about 50% of the infected individuals. About 20% of the individuals suffering from chronic hepatitis C show histological signs of hepatic cirrhosis. In addition to this, hepatitis C virus probably plays an important part in the development of hepatocellular carcinomas. These complications often lead to death. The medicinal treatment of hepatitis C is still in the experimental stage. Usually, individuals suffering from chronic hepatitis C are treated by dietetic measures in order to spare the hepatic metabolism. The use of α-interferon and ribavarin is also considered. However, these agents often show undesired side-effects, and moreover both are very expensive. Furthermore, both preparations show a lasting effect in only about 20% of the patients.

SUMMARY OF THE INVENTION

The present invention was therefore based on the technical problem of providing further substances or combinations which show an improved effect in the treatment of diseases caused by hepatitis C virus.

This task is achieved by the use of at least one hydrolytic enzyme and at least one flavonoid.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiment(s) which are presently preferred. It should be understood, however, that the invention is not limited to the precise arrangements and instrumentalities shown. In the drawings.

DETAILED DESCRIPTION OF THE INVENTION

Figure 1:
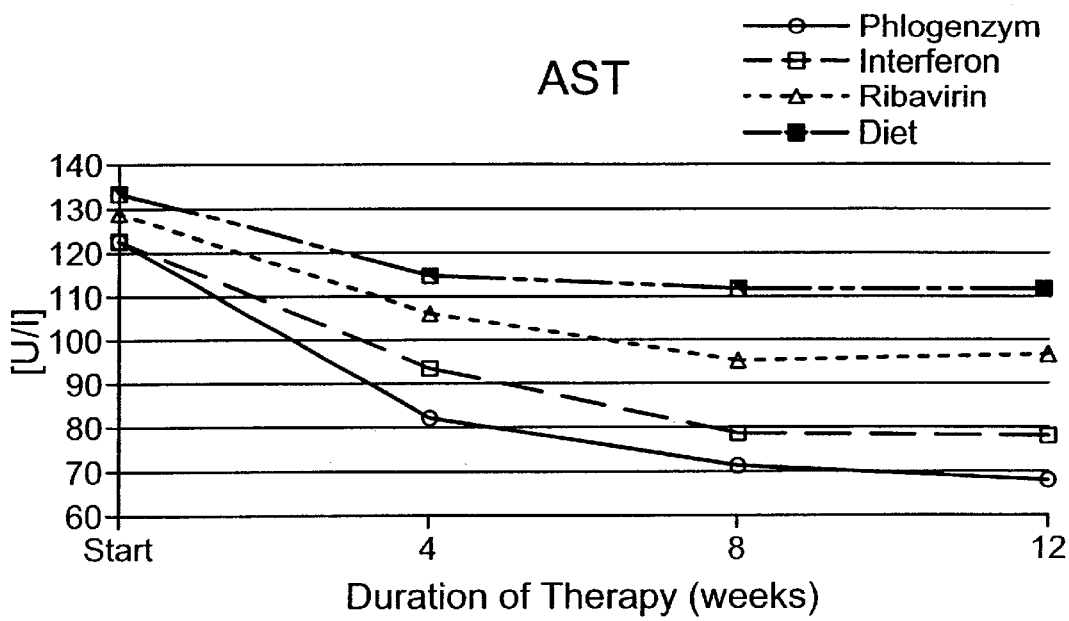
FIGS. 1–3 are graphs of data obtained by monitoring the function of liver transaminases (AST, ALT and S-γ-GT, respectively), wherein the transaminase values in enzyme units per liter (U/l) are plotted against the duration of therapy in weeks for each of four different types of treatment.

Hydrolytic enzymes are grouped together under the generic term "hydrolases." These enzymes are capable of cleaving substrates by the incorporation of water. In the IUBMB system of nomenclature, they constitute the third enzyme class. They include esterases, glycosidases, ether hydrolases, the large group of peptidases (proteases), and also enzymes which break bonds between carbon and nitrogen (amidases, amidinases, nitrilases), acid anhydride bonds, carbon-carbon bonds, carbon-halogen bonds, phosphorus-nitrogen bonds, sulphur-nitrogen bonds, and carbon-phosphorus bonds with hydrolysis.

Preferred among these hydrolases are proteases. These enzymes catalyse the hydrolytic cleavage of the peptide bond in proteins and peptides. Proteases include proteinases and peptidases. Examples of proteases which can be used in the present invention are chymotrypsin, elastase, cathepsins, pepsin, plasmin, trypsin, bromelain and papain. Among these, bromelain, trypsin and papain are preferred.

The preferred enzymes according to the invention can be economically isolated from the following raw materials.

Bromelain is a proteolytically active enzyme from the pressed-out juice of the pineapple and can also be isolated from ripe fruit.

Papain is a proteolytic enzyme which is produced from the milky juice of the unripe, fleshy fruit of the melon tree Carica Papaya. Pure papain is a crystalline polypeptide with a molecular weight of 23,350, which consists of a chain of 212 amino acid residues with four disulphide bridges: sequence and three-dimensional structure are known. Papain is used in many ways: owing to its protein-cleaving properties, as a "meat tenderizer" or "tenderizing salt," for clarifying beer, for bread and biscuit manufacture, in leather preparation, in the textile industry, for degumming silk and for preventing wool felting, in the tobacco industry for improving quality, for recovery of silver from used photographic material, and also in bacteriology for peptone production. In medicine, papain is already used for supporting enzymatic digestion, for enzymatic wound-cleaning and as an additive for denture cleaning agents. For special purposes, papain preparations are also supplied bound to plastic polymers or agarose supports. Papain has also been used as a catalyst for synthesis of oligopeptides.

Trypsin is a proteolytic enzyme which is formed in the pancreas, and in combination with other enzymes is already used therapeutically. It is among the serine proteinases. Crystalline trypsin has a molecular weight of about 23,300, is soluble in water, but not in alcohol, has an activity optimum at pH 7 to 9 and cleaves peptide chains specifically on the carboxy side of the basic amino acid residues L-lysine and L-arginine. The three-dimensional structure of trypsin, which consists of 223 amino acids, is known.

Particularly good activity is seen with the use of a combination of the enzymes bromelain, papain and/or trypsin. These enzymes are used according to the invention in combination with at least one flavonoid.

Flavonoids, which occur in all higher plants, are important phenylpropane derivatives with the C15 basic skeleton of flavan. They occur mainly water-soluble in glycosylated form in the vacuoles of plant cells and are often esterified with aliphatic and/or aromatic acids, e.g., with malonic acid or caffeic acid. Non-glycosylated lipophilic flavonoids occur as non-volatile components in ethereal oils, accumulate in the wood parenchyma or are secreted onto the epidermis of leaves. The aglycones of the flavonoids are subdivided into the following classes on the basis of the oxidation level of their central pyran ring: anthocyanidines, aurones, catechins, chalcones, desoxyanthocyanidines, flavonols, flavanones, flavolones, flavones, isoflavones and leucoanthocyanidines. A preferred flavonoid is rutoside, a pentahydroxyflavone derivative with a molecular weight of 610. Especially preferred is rutoside in the form of the acid sodium salt. However, synthetic rutoside derivatives such as troxserutin and monoxerutin can also be used. Apart from rutoside, preparations made from Ginko biloba can also be used.

It is assumed—without being tied to one theory—that a metabolite of the rutoside, such as quercetin, displays the pharmacological activity. Preparations from Ginko biloba yield similar metabolites.

As well as the remarkable and unexpected action of the combination of at least one hydrolytic enzyme and at least one flavonoid in the treatment of hepatitis C virus diseases, the combined use also has the advantage that even with prolonged use no harmful side-effects occur.

The combined use of 90 mg bromelain, 48 mg trypsin and 100 mg rutoside is of especially good efficacy.

The combination according to the invention can also be used together with other virostatic agents. In particular, α-interferon and/or ribavirin can be used for this.

α-Interferon is a protein of the cytokine group, which has antiviral, but non-virus specific activity. Preferably, 1 million to 6 million I.U. α-interferon are used 1 to 7 times per week.

Ribavirin is a synthetic nucleoside with a broad spectrum of activity as a virostatic agent. Preferably, 1000 mg to 1500 mg ribavirin daily are used, and especially preferably 1200 mg.

The combination according to the invention can further be used with all normal additives and/or carriers.

All the normally used substances are possible as additives and carriers, e.g. fillers, binders, thickeners, adsorbents, drying agents, gelling agents, film-foaming agents, absorbents, lubricants, mold release agents, disintegration aids, disintegrants, antioxidants, preservatives, flavor and aroma correctors and colorants. These substances can be used in the usual amounts. Illustrative examples are sugar and sugar alcohols such as lactose, sucrose, glucose, mannitol and sorbital, macromolecular additives such as starches, cyclodextrins, gelatines, tragacanth, pectin, cellulose, methylcellulose, polyacrylates, polyvinyl alcohol, macrogels and polyethylene oxide, surfactant additives such as sodium dodecylsulphate, lecithin, fatty alcohols and sterols, inorganic additives such as talc, white clay, bentonite, $TiO_2$, $CaHPO_4$, $CaCO_3$, $NaHCO_3$ and $SiO_2$, and organic additives such as vanillin, dibutyl phthalate, polyindone, yellow wax, shellac and camauba wax. Preferably the use according to the invention is by oral administration, however all other normal presentations are also possible. The following examples further illustrate the invention.

80 patients suffering from hepatitis C were divided into four parallel groups. Group 1 received two tablets of Phlogenzym (registered trade-mark) orally three times daily. Each tablet of Phlogenzym contains 90 mg bromelain, 48 mg trypsin and 100 mmg rutoside.

Group 2 received α-interferon, and group 3 ribavirin. Group 4 received a liver-supporting dietetic treatment (vitamins and minerals). Each patient was treated for 12 weeks.

None of the patients was suffering from hepatitis A, B or D or another liver disease, The patient groups, and hence the efficacy of the medication, were monitored by following the function of the liver transaminases AST (aspartate aminotransferase), ALT (alanine aminotransferase) and S-γ-GT (serum γ-glutamyl transpeptidase).

Figure 2:
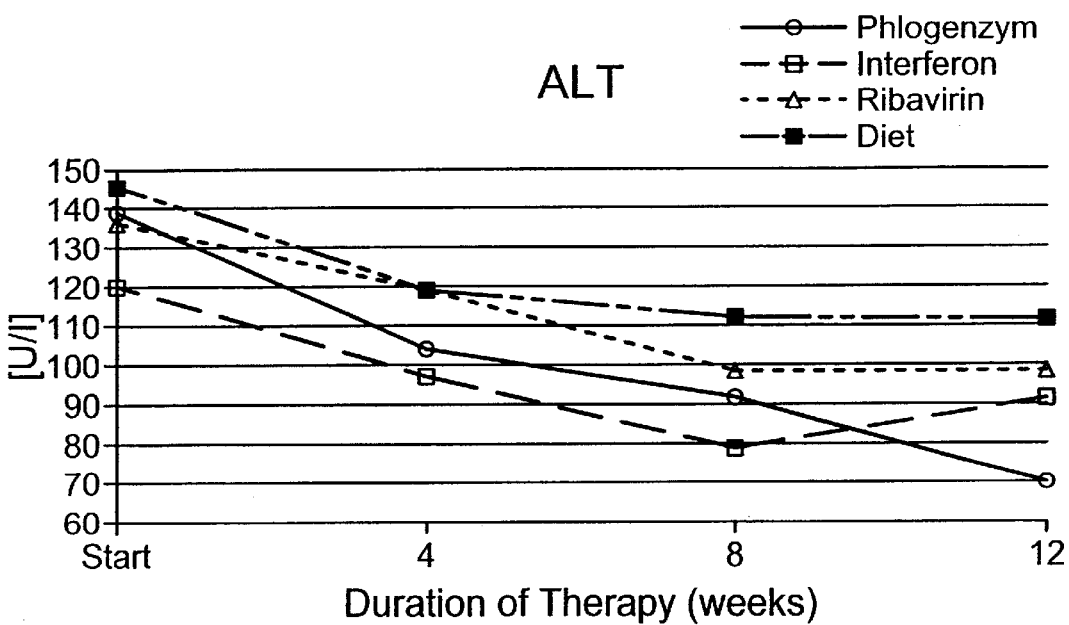
Figure 3:
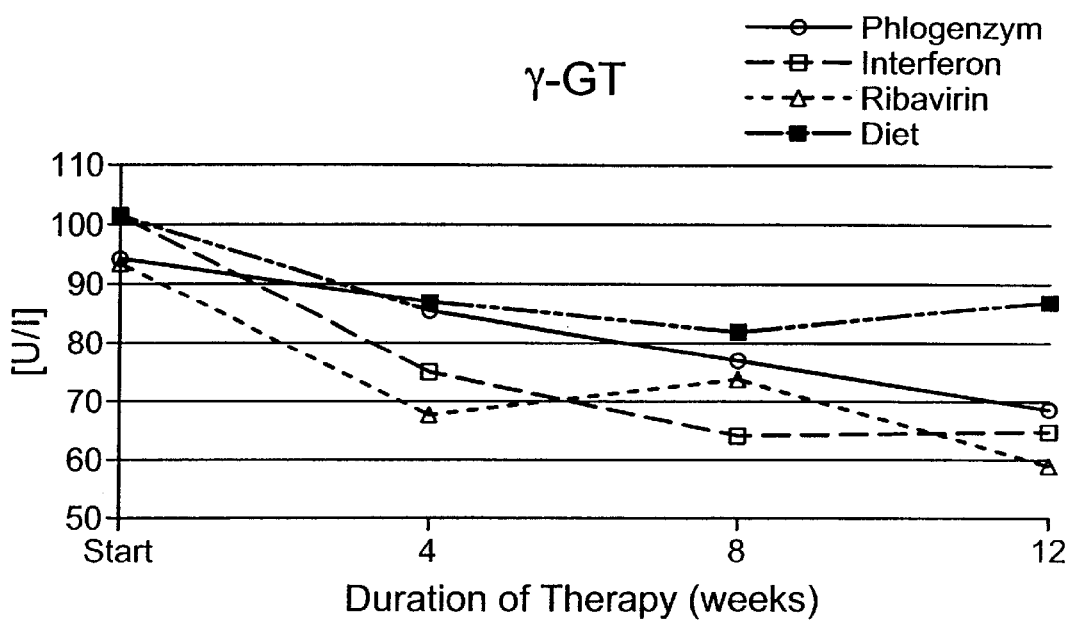

These data are presented in graph form in FIGS. 1 to 3.

The values for the function of the transaminases fell from pathological ranges in all 4 groups. The improvement in the group which received the dietetic treatment was the smallest. The group which received only ribavirin also showed only a slight improvement. A significant improvement was only achieved in the groups which received α-interferon or Phlogenzym. However, only the Phlogenzym patient group showed a continual improvement. With the use of α-interferon, a deterioration or at least stagnation was again observed in each case after 8 weeks. The combination of Phlogenzym and α-interferon or ribavirin also showed good efficacy.

Figure 4:
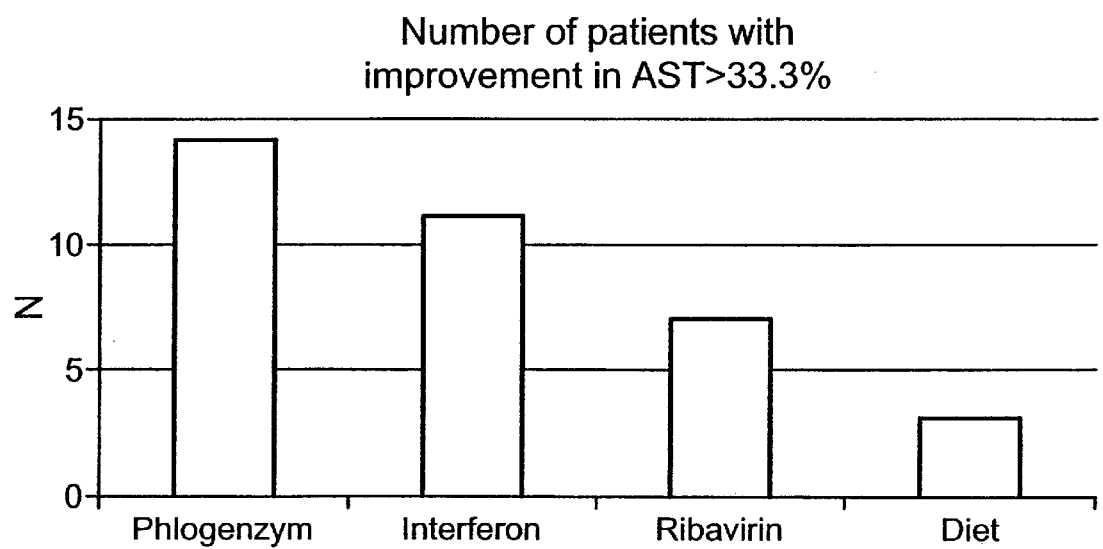
FIGS. 4–6 are bar graphs of the number of patients (N) showing greater than 33.3% improvement in the liver transaminase functions which were monitored according to FIGS. 1–3, respectively, for each of the four treatments.
Figure 5:
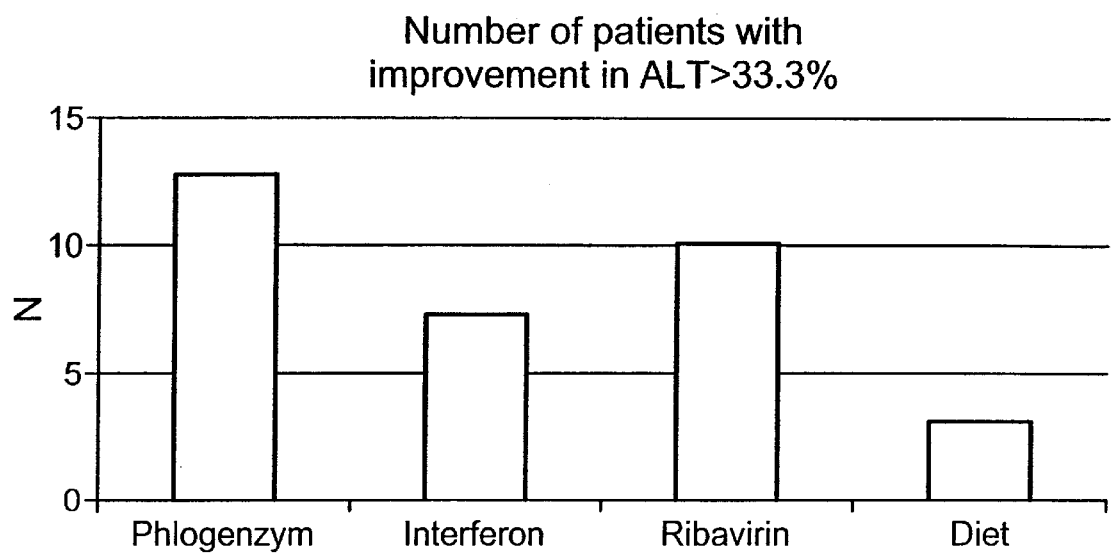
Figure 6:
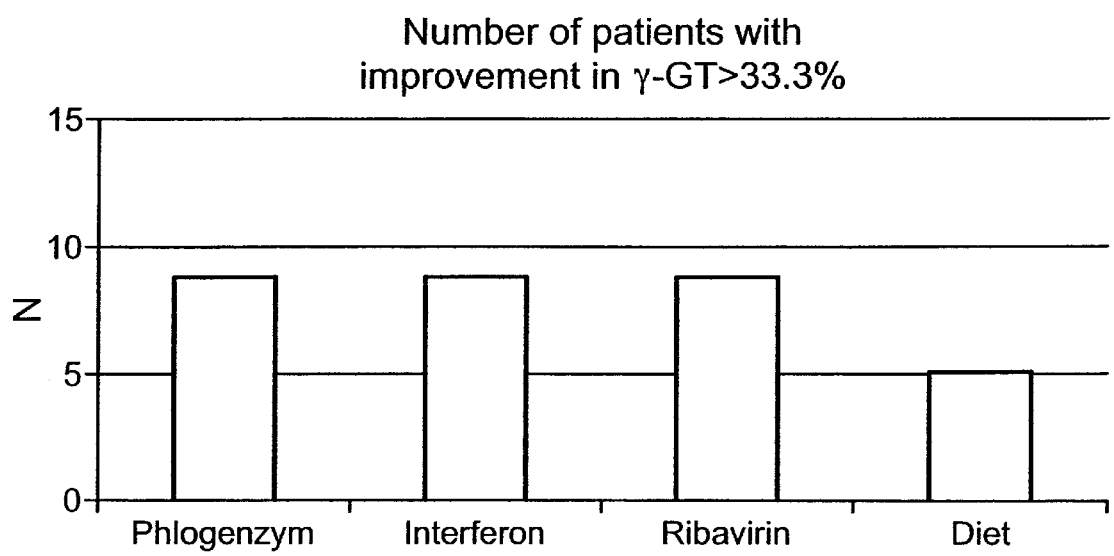

Extrapolation of these results indicates that a longer treatment with Phlogenzym could result in a still more marked improvement, If the number of patients from each group whose values improved by more than ⅓ from the starting value is calculated, the difference between the 4 groups becomes still clearer. These calculations are shown graphically in FIGS. 4–6. It can clearly be seen that the treatment with Phlogenzym is the most effective treatment.

Figure 7:
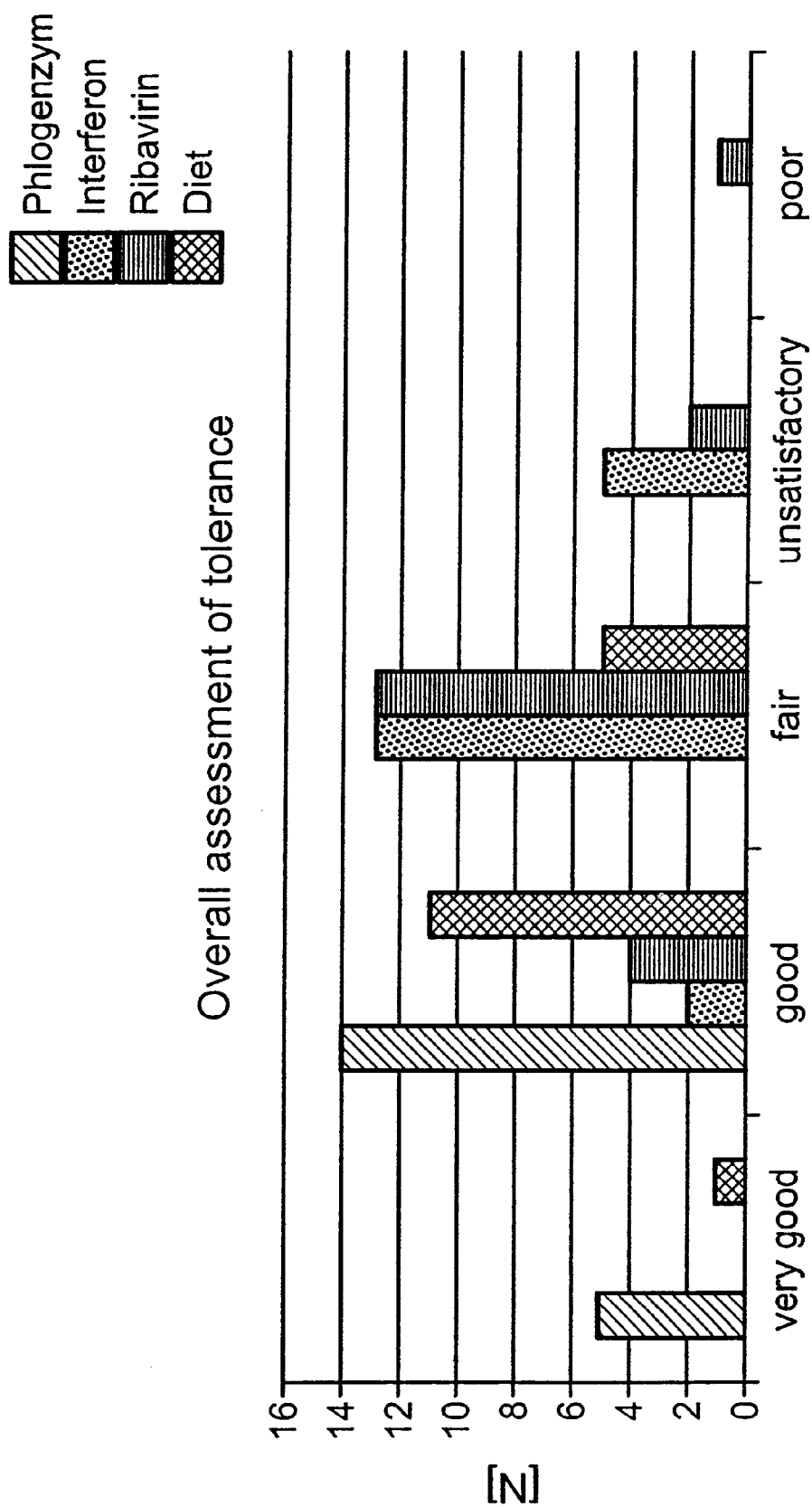
FIG. 7 is a bar chart illustrating the results of a tolerance evaluation of patients receiving the four different treatments whose results are shown in FIGS. 1–3 and 4–6.

If the assessment of tolerance (shown in FIG. 7) is also included in the evaluation, the difference between the treatment with Phlogenzym and the other monotherapies becomes even clearer. At the end of the therapy, all patients who were treated with Phlogenzym assess the tolerance as "very good" or "good." PCR measurements have moreover shown that in the Phlogenzym patients a decrease of about 50% in the viral burden could be observed.

It will be appreciated by those skilled in the art that changes could be made to the embodiment(s) described above without departing from the broad inventive concept thereof. It is understood, therefore, that this invention is not limited to the particular embodiment(s) disclosed, but it is intended to cover modifications within the spirit and scope of the present invention as defined by the appended claims.

We claim:

1. A method of treating a Hepatitis C virus infection, the method comprising administering to a patient infected with the virus at least one proteolytic enzyme and at least one flavonoid selected from the group consisting of rutoside, rutoside derivatives, metabolites of rutoside, and preparations of Gingko Biloba.

2. The method according to claim 1, wherein the proteolytic enzyme is selected from the group consisting of trypsin, bromelain and papain.

3. The method according to claim 1, wherein the flavonoid comprises rutoside.

4. The method according to claim 1, wherein the treatment comprises administering 20 to 100 mg bromelain, 10 to 70 mg trypsin, and 80 to 120 mg rutoside per dosage unit.

5. The method according to claim 1, further comprising administering α-interferon and/or ribavirin.

6. The method according to claim 1, wherein the patient is suffering from chronic hepatitis C.

* * * * *